US006841393B2

(12) United States Patent
Koenig

(10) Patent No.: US 6,841,393 B2
(45) Date of Patent: Jan. 11, 2005

(54) SELECTIVE REMOVAL OF CONTAMINANTS FROM A SURFACE USING COLORED PARTICLES AND ARTICLES HAVING MAGNETS

(75) Inventor: David W. Koenig, Menasha, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 232 days.

(21) Appl. No.: 10/160,575

(22) Filed: May 31, 2002

(65) Prior Publication Data

US 2003/0007942 A1 Jan. 9, 2003

Related U.S. Application Data

(63) Continuation-in-part of application No. 09/420,472, filed on Oct. 19, 1999, now Pat. No. 6,503,761.

(51) Int. Cl.[7] .................................................. G01N 33/553
(52) U.S. Cl. .................... 436/526; 436/518; 436/530; 436/531; 436/532; 436/533; 436/541; 436/72; 436/73; 436/806; 424/484; 424/489; 424/490; 424/443; 424/447; 424/449; 424/9.8; 435/7.1; 435/7.2; 435/7.4; 435/7.32; 435/30; 435/32; 435/34; 428/283
(58) Field of Search ........................... 436/526, 518, 436/530, 531, 532, 533, 538, 541, 72, 73, 806; 424/484, 489, 490, 443, 447, 449, 9.8; 435/7.1, 7.2, 7.4, 7.32, 30, 32, 34; 428/283

(56) References Cited

U.S. PATENT DOCUMENTS 3,970,518 A 7/1976 Giaever
4,201,827 A 5/1980 Heitkamp
4,225,580 A 9/1980 Rothman et al.

(List continued on next page.)

FOREIGN PATENT DOCUMENTS

| DE | 36 29 761 | 3/1987 |
| FR | 2 268 512 | 11/1975 |
| FR | 2 400 883 | 3/1979 |
| JP | 3019948 | 1/1999 |
| WO | WO 01/28511 | 4/2001 |
| WO | WO 01/28512 | 4/2001 |

OTHER PUBLICATIONS

J. Kandzia et al.; "Cell Separation: Comparison Between Magnetic Immuno–Microspheres (MIMS) and FACS"; Proceedings of the International Meeting, Rostock, German Democratic Republic, Sep. 24–28,1984; *Cell Electrophoresis:* 1985: pp. 87–93.

(List continued on next page.)

*Primary Examiner*—Christopher L. Chin
*Assistant Examiner*—Pensee T. Do
(74) *Attorney, Agent, or Firm*—Pauley Petersen & Erickson

(57) ABSTRACT

A system and method for removing contaminants from a surface. The system is designed to use very small particles having means thereon which are capable of selectively binding to a contaminant or contaminants of interest. The particles may contain a dye to render the particles visible in order for a user to observe the application and removal of the particles. The particles also have magnetic properties which may be provided by a high iron content. A carrier can be used to apply the particles to a surface whereupon the targeted contaminants bind to the particles. The particles may then be readily removed from the surface using magnets. When the particle is removed, the targeted contaminants are also removed. The invention is especially useful for the removal of contaminants from skin.

72 Claims, 2 Drawing Sheets

U.S. PATENT DOCUMENTS

| | | | |
|---|---|---|---|
| 4,230,685 A | 10/1980 | Senyei et al. | |
| 4,452,773 A | 6/1984 | Molday | |
| 4,454,234 A * | 6/1984 | Czerlinski | 436/526 |
| 4,537,767 A | 8/1985 | Rothman et al. | |
| 4,672,040 A | 6/1987 | Josephson | |
| 4,677,055 A | 6/1987 | Dodin et al. | |
| 4,677,067 A | 6/1987 | Schwartz et al. | |
| 4,873,102 A | 10/1989 | Chang et al. | |
| 4,965,007 A | 10/1990 | Yudelson | |
| 5,000,203 A | 3/1991 | Hamada | |
| 5,160,725 A | 11/1992 | Pilgrimm | |
| 5,187,209 A | 2/1993 | Hirai et al. | |
| 5,415,997 A | 5/1995 | Atrache et al. | |
| 5,445,971 A | 8/1995 | Rohr | |
| 5,468,529 A | 11/1995 | Kwon et al. | |
| 5,492,754 A | 2/1996 | Chen | |
| 5,516,531 A | 5/1996 | Makino et al. | |
| 5,518,890 A | 5/1996 | Starkweather et al. | |
| 5,536,644 A | 7/1996 | Ullman et al. | |
| 5,576,185 A | 11/1996 | Coulter et al. | |
| 5,607,667 A | 3/1997 | Holcomb | |
| 5,637,165 A | 6/1997 | Chen | |
| 5,658,583 A | 8/1997 | Zhang et al. | |
| 5,665,582 A | 9/1997 | Kausch et al. | |
| 5,695,946 A | 12/1997 | Benjamin et al. | |
| 5,741,336 A | 4/1998 | Fraser | |
| 5,800,835 A | 9/1998 | Zastrow et al. | |
| 6,027,945 A | 2/2000 | Smith | |
| 6,066,673 A | 5/2000 | McIver et al. | |
| 6,107,261 A | 8/2000 | Taylor et al. | |
| 6,126,588 A | 10/2000 | Flamant et al. | |
| 6,136,549 A | 10/2000 | Feistel | |
| 6,146,324 A | 11/2000 | Engel | |
| 6,503,761 B1 * | 1/2003 | Koenig et al. | 436/526 |

OTHER PUBLICATIONS

M. Markiewicz et al.; Immunomagnetic Method of CD34(+) Cell Separation; *Transplantation Proceedings;* Vol. 28, No. 6; December 1996; pp. 3526–3527.

Per Arne Risoen et al.; One–Step Magnetic Purification of Recombinant DNA–Binding Proteins Using Magnetizable Phosphocellulose: *Protein Expression and Purification:* Vol. 6, No. 3, June 1995; pp. 272–277.

A.I. Autenshlyus et al.; Magnetic–sensitive dextran–ferrite immunosorbents (for diagnostic and therapy); *Journal of Magnesium and Magnetic Materials*; Vol. 122. Nos. 1–3; April 1993; pp. 360–363.

A.M.A. Carneiro Leao et al.; "Immobilization of Protein on Ferromagnetic Dacron"; *Applied Biochemistry and Biotechnology:* Vol. 31, ISSN: 0173–2289; pp. 53–58.

J. E. Davies et al.: "A Comparison of the Use of Two Immunogenic for Secondary Purification of Pancreatic Islets"; *Transplanation:* Vol. 62, No. 9, Nov. 15, 1996; pp. 1301–1306.

R. Alan Hardwick et al.; "Design of Large–Scale Separation Systems for Positive and Negative Immunomagnetic Selection of Cells Using Superparamagnetic Microspheres"; *Journal of Hematotheraphy;* Vol. 1, No. 4, Winter 1992.

Anders Hedrum et al.; "Immunomagnetic Recovery of *Chlamydia trachomaris* from Urine with Subsequent Colorimetric DNA Detection", *PCR Methods an dApplications:* Vol. 2, No. 2, November 1992; pp. 167–171.

Heidi A. Israel; "Immunomagnetic separation: A tool for microbiology"; *American Biotechnology Laboratory;* Vol. 12., No. 6, May 1994; pp. 50 and 52.

Sumner Levine; "Magnetic Techniques for in vitro Isolation of Leucocytes"; *Science,* Vol. 123, No. 3184; Jan. 6, 1956; pp. 185–186.

Xiaohong Li et al.; "Synthesis of Magnetic Polymer Microspheres and Application for Immobilization of Proteinase of *Balillus sublitis"; Journal of Applied Polymer Science;* Vol. 58, No. 11, Dec. 12, 1995, pp. 1991–1997.

Leonid B. Margolis et al.; "Magnetoliposomes: Another Principle of Cell Sorting"; *Biochimica Et Biophysica Acta* (International Journal of Biochemistry and Biophysics); 1983; pp. 193–195.

Tadashi Matsunaga et al.; "Chemiluminescence Enzyme Immunoassay Using Baterial Magnetic Particles"; *Analytical Chemistry,* Vol. 68, No. 20, Oct. 15, 1996; pp. 3551–3554.

Noriyuki Nakamura et al.; "Detection and Removal of *Escherichia coli* Using Fluorescein Isothiocyanate Conjugated Monoclonal Antibody Immobilized on Bacterial Magnetic Particles"; *Analytical Chemistry,* Vol. 65, No. 15; Aug. 1, 1993; pp. 2036–2039.

P. Ndhlovu et al.; "Optimization of the Magnetic Bead Antigen Capture Enzyme Immuno Assay for the detection of circulating anodic antigens in mixed Schistosoma infections"; *Acta Tropica,* Vol. 59, issue 3, (1995).

J. Plavins et al.; "Study of colloidal magnetite–binding erythrocytes: Prospects for cell separation"; *Journal of Magnetism and Magnetic Materials,* Vol. 122, Nos. 1–3, April 1993; pp. 349–353.

Patrick M. Regan et al.; "Development fo a nucleic acid capture probe with reverse transcriptase–polymerase chain reaction to detect poliovirus in groundwater"; *Journal of Virological Methods,* Vol. 64, 1997; pp. 65–72.

J.G. Treleaven et al.; "Removal of Neuroblastoma Cells from Bone Marrow with Monoclonal Antibodies Conjugated to Magnetic Microspheres"; *The Lancet,* Jan. 14, 1984; pp. 70–73.

Mirka Safarikova et al.: "Magneticke Separace V Prirodnich Vedach A Biotechnologiich", *Chemicke listy 5;* 1995; pp. 269–336 (NO TRANSLATION AVAILABLE)

Dennis E. Vaccaro, "Applications of magnetic separation: Cell sorting"; *American Biotechnology Laboratory;* Vol. 8, No. 5, April 1990; pp. 3030, 32–35.

John A. Oberteuffer, "Magnetic Separation: A Review of Principles, Devices, and Applications"; *IEEE Transactions on Magnetics,* Vol. MAG–10, No. 2, June 1974; pp. 223–238.

Hancock et al.; "A rapid and highly selective approach to cell separations using an immunomagnetic colloid"; *Journal of Immunological Methods;* 164 (1993); pp. 51–60.

Gupia et al.; "Magnetically Controlled Targeted Micro–Carrier Systems"; *Life Sciences;* Vol 44; No. 3; 1989; pp. 175–186.

Safarik et al.; "The application of magnetic separations in applied microbiology"; *Journal of Applied Bacteriology:* 1995; 78; pp. 575–585.

Widder et al.; "Specific Cell Binding Using Staphylococcal Protein A Magnetic Microspheres"; *Journal of Pharmaceutical Sciences;* Vol. 70. No. 4; April 1981; pp. 387–389.

Vaccaro et al.; "Use of Monoclonal Antibodies with Magnetic Particles to Separate Cell Subpopulations by Positive Selection"; *Methods in Molecular Biology;* Vol. 45; Monoclonal Antibody Protocols; pp. 253–259.

Rye et al.; "Immunobead Filtration: A Novel Approach for the Isolation and Propagation of Tumor Cells"; *American Journal of Pathology;* Vol. 150, No. 1; January 1997.

Pope et al.; "Evaluation of magnetic alginate beads as a solid support for positive selection of CD34+ cells", *Journal of Biomedical Materials Research* Vol. 28, (1994) pp. 449–457.

* cited by examiner

SELECTIVE REMOVAL OF CONTAMINANTS FROM A SURFACE USING COLORED PARTICLES AND ARTICLES HAVING MAGNETS

This application is a continuation-in-part of Ser. No. 09/420,472, filed on Oct. 19, 1999 now U.S. Pat. 6,503,761.

FIELD OF THE INVENTION

The present invention is directed to a system and method whereby contaminants may be selectively bound to colored particles and removed from skin using magnets.

BACKGROUND OF THE INVENTION

Humans have vast amounts of debris and microbes existing in their bodily fluids and on their skin. Many of the microbes are beneficial to the health and well-being of the individual. However, many of these microbes are contaminants which are not beneficial. Many of these non-beneficial microbes exist in body fluids which contact the skin, such as tears, perspiration, oils, nasal secretions, and bodily waste. The microbes may also exist in wounds. These microbes, along with debris contaminants, may irritate the skin causing a variety of skin problems such as rashes, breakouts, clogged pores, or discoloration of the skin or, in the case of wounds, may slow down the rate at which the wound will heal.

Many different products have been produced to help eliminate the problems associated with debris and non-beneficial microbes. Various cleaning products include detergents which effectively remove excess oils and fluids, thereby reducing the number of both beneficial and non-beneficial microbes. However, the cleaning products that simply reduce the number of microbes leave behind some of the non-beneficial microbes such that the non-beneficial microbes still exist on the skin, just in lower numbers. Additionally, if too much oil is removed from the skin, then dryness of the skin could result.

Other products have introduced microbiocides which are effective at killing all microbes on the skin. However, since these microbiocides eliminate beneficial microbes as well as non-beneficial microbes, these products destroy beneficial skin ecology and thus have a negative impact on skin health.

Accordingly, what is needed is a system and method of removing debris and non-beneficial microbes from skin without removing beneficial microbes to help reduce the occurrence of skin problems associated with non-beneficial microbes while maintaining skin health.

SUMMARY OF THE INVENTION

The present invention is directed to a system and method of removing microbial contaminants from skin. The system utilizes receptor materials which selectively bind to the microbe or microbes of interest. The receptor materials are placed on the surface of the skin wherein they attach to and bind the microbes. Then, the receptor material and bound microbes are removed from the skin. This allows non-beneficial microbes, such as bacteria, yeast, toxins, enzymes, and/or debris, to be removed while beneficial microbes remain, thereby maintaining skin health or expediting the healing of wounds.

The system includes particles having a magnetic element, such as iron or cerium, suitably up to 90% by weight of the magnetic element, and receptor materials for selectively binding a microbial contaminant on the skin surface. The particles should be relatively small in size, suitably having a diameter of less than about 25 microns. These particles are designed to be placed on the skin wherein the receptor materials, such as ligands, may bind to the desired contaminants. Alternatively, the particles may electrostatically interact with the surface contaminants, thereby binding the contaminants to the particles. Then, means are provided which remove the particles and the accompanying receptor material and microbial contaminants from the surface of the skin.

Means for removing the particles, the accompanying receptor material, and microbial contaminants suitably include magnets. More specifically, after the microbial contaminants are bound to the magnetic particles, articles having magnets contained therein or thereon may be used to remove the magnetic particles from the skin. Examples of suitable magnet-containing articles include nonwoven fabrics, woven materials, bandages, diapers, adhesive strips, facial tissues, personal care products, wipes, and feminine articles.

The particles may be applied to the skin within a lotion, a cream, a spray, a solution, a non-magnetic cellulose wipe, a non-magnetic polymeric wipe, or using any other suitable carrier.

In one embodiment of the invention, the particle may also include a dye, thus making the particles more visible. By using colored particles, the cleaning action on the surface can be seen.

With the foregoing in mind, it is a feature and advantage of the invention to provide a system that can selectively attach and remove desired microbes while permitting beneficial microbes to remain on the skin.

DETAILED DESCRIPTION

Figure 1:
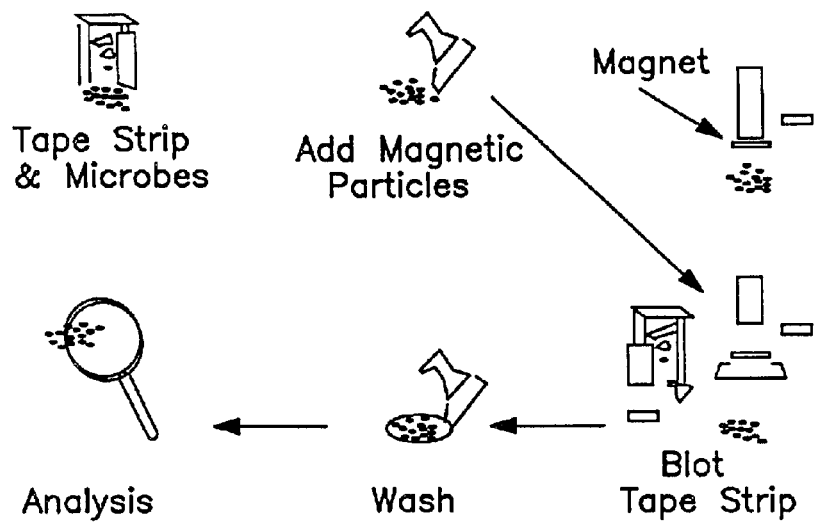
FIG. 1 outlines the test procedure by which an embodiment of the present invention was used to determine the effectiveness of the magnetic test strips.

The present invention is directed to a system and method for removing contaminants from skin. The system may be used to remove a wide range of microbial contaminants, such as bacteria, yeast, toxins, enzymes, and/or debris.

The system includes one or more particles that bind to contaminants of interest. The particles may include ligands, electrostatic charge, or any other suitable means for selectively binding a contaminant on the skin surface. The term "selectively bind," as used herein, refers to the ability of particles to adhere to certain intended contaminants and not adhere to certain other non-intended materials. The particles also include magnetic properties. Once the selected microbial contaminants are bound to the particles, the particles and the bound contaminants can be removed from the skin using a magnetic force to attract the magnetic properties of the particle while leaving behind beneficial microbes on the skin to maintain skin health.

The particles in the system are suitably non-toxic and, desirably, are capable of binding a ligand thereto. Suitable particles include those made from natural polymers, random copolymers, and/or plastics. Representative examples include natural polymers such as cellulose; random copolymers such as polybutylene copolymer, polyethylene, polypropylene copolymers, polyethylene elastomers; and plastics such as polystyrene, polyethylene, polypropylene, rayon, nylon, polyvinylidine chloride, and polyesters; chitin; starch; dextran; and modified-starch. Silica could be used as an inorganic particle. Other inorganic particles might include clays. The type of particle used may vary depending on several considerations, including the intended use or the contaminant to be removed. The size of the particle may also vary depending on the intended use or the product in which the particle is to be used. However, if the particle is too large, it may aggravate the skin as it is applied. Therefore, in general, the particles are relatively small in size. Suitably, the particles are less than about 25 microns in diameter, or between about 0.01 and about 20 microns in diameter, or between about 0.01 and about 10 microns in diameter, with "diameter" referring generally to a thickness or width of the particles since the particles may be irregularly shaped, or otherwise not necessarily spherical.

The particles may be rendered magnetic through the inclusion of a magnetic metal element, such as iron or cerium. Other suitable magnetic materials that may magnetize the particles include Neodymium Iron Boron (NdFeB or NIB), Samarium Cobalt (SmCo), Alnico, and ceramic materials. The amount of iron or cerium, or other magnetic material, contained within each particle may vary depending on the amount of charge desired, the overall size of the particle, the carrier within which the particles will be applied to the skin, if any, and the location and number of magnets used to remove the particle. However, in general, the particles may include from about 10% to about 90%, or from about 20% to about 80%, magnetic material by weight of the particle. Thus, each particle may have a magnetic mass susceptibility of from about 50,000,000 to about 200,000,000 $m^3/kg$.

Once the desired particle type, size and magnetic content have been selected, the particle may be modified to include means for selectively binding a contaminant on the skin surface. Such modification may be in the form of attaching a ligand to the particle, or charging the particle to obtain the desired polarity to attract the selected contaminant through electrostatic interaction. The choice of ligand or charge depends upon the type of contaminant to be removed and, for further consideration, may affect the composition of the particle. If a charge is used, the charge may either be a positive charge or a negative charge. If a ligand is used, it may be selected from a wide variety of useful ligands.

A positively charged particle is capable of being used to bind and remove yeast and bacteria (negatively charged) and virtually any negatively charged molecule. Examples of particles useful as positively charged particles include, but are not limited to, chitin, diethylaminoethyl, ciethyl[2-hydroxypropyl]aminoethyl, polyethyleneimine, triethylaminohydroxypropyl, quaternary ammonium, quaternary alkylamine, quaternary alkylanolamine, trimethylbenzylammonium, dimethylethanolbenzylammonium, polyamine, alkylamine, dimethylethanolamine, octadecyldimethyltrimethoxylsilpropylammonium chloride, and kymene.

A negatively charged molecule may be used to bind and remove protein and other biological contaminates, not including yeast or bacteria. Examples of particles useful as negatively charged particles include, but are not limited to, carboxymethyl cellulose, sulfopropyl cellulose, cellulose phosphate, DOWEX®, DUOLITE®, AMBERLITE®, and bentonite.

A positive or negative charge may be given to the particle by at least two methods. One would be to use material that already has the appropriate charge. For example, cellulose could be used to impart an overall negative charge to the particle. Conversely, chitin could be used to impart an overall positive charge to the particle. The second method would be to modify the materials by chemical means to change the charge characteristic of the surface. For example, addition of amines would impart a positive charge, while addition of carboxyl groups would impart a negative charge.

Native silanol groups on the surface of silica microspheres are readily reacted with aqueous or solvent-based silane coupling agents to yield preactivated silica microspheres with a large variety of surface functional groups. Examples include chloromethyl, carboxyl, and amino groups. Oligonucleotides can be covalently bound to surface-modified silica via the 5'-amino end. Lipids can be bound via the carboxyl group on the fatty acid chain and propylamine surface groups on the silica.

As indicated, the use of ligands is another appropriate means for selectively binding a contaminant. In one embodiment, the particles are reactive superparamagnetic monodispersed microspheres (SMM) that are coated with ligands to specifically bind the target microbes.

A large number of ligands may be used in the invention, including plant lectins and antibodies, among others. Furthermore, extracts of plants and natural products may also be used.

Plant lectins useful in the invention include, but are not limited to, lentil lectin, wheat germ lectin, dolichos biflorus, galanthus nivalis, glycine max, heli pomatia, lens culinaris, phaseolus vulgaris, phytolacca americana, ulex europaeus, and vicia villosa. These lectins are effective at removing microbial materials, particularly any cells with mannopyranosyl or glucopyranosyl residues on the membrane surface. These lectins may also help in the removal of proteins or skin debris with similar characteristics. Other microbes which may be removed by plant lectins include those having glucose, mannose, or n-acetyl-glucosaminyl residues in the microbe cell wall and other skin debris material.

Other ligands which may be used in the invention include *dolichos biflorus, galanthus nivalis, glycine max, hell pomatia, lens culinaris, phaseolus vulgaris, phytolacca americana, ulex europaeus*, and *vicia villosa*.

Antibodies useful in the present invention include those having specific antibodies for any microbe-associated cell wall or membrane component. Other ligands useful in the present invention include those that use cell surface receptors specific for microbes. These include, but are not limited to, *Staphylococcus, Steptococcus, Candida*, and *Propionibacterium*. All of these are specific for cell surface receptors which bind glycosides. Such glycosides could be attached to the magnetic particle.

If a ligand is used as the means for binding the contaminant, then the ligand must be attached to the particle such that when the particle is applied to the skin, the ligand is able to bind with the contaminant or contaminants of choice and remove these contaminants when the particle is removed from the skin. There are a plurality of known methods which may be used to attach the ligand to the particle, most notably direct adsorption and covalent attachment.

Direct adsorption involves adsorbing the ligand onto the surface of the particle. Simply adsorbing protein, especially polyclonal IgG, on the surface of polystyrene microspheres is successful more than 95% of the time. For maximum surface coverage (up to a monolayer), buffer pH should be at, or slightly more basic than, IgG's isoelectric point (that is, pH 8), where the protein is in its most relaxed, compact form. Tris buffer (pH 8.0) and phosphate buffer (pH 7.4) work well. The Fc and Fab portions of IgG adsorb differently in response to pH changes. A slightly alkaline pH optimizes adsorption of the Fe portion and ensures relative suppression of Fab adsorption.

As an alternative to simple adsorption, IgG and serum albumin (human or bovine) can be mixed and then adsorbed simultaneously. One commercial protocol calls for a weight ratio of 1 IgG to 10 albumin in the coadsorption mixture.

Adsorption can be followed by glutaraldehyde cross-linking of the mixed proteins on the microsphere surface.

In covalent bonding, the ligand is covalently bonded to the particle. For example, haptens and other low-molecular-weight labels, which on their own might not adsorb well or remain attached, can be covalently bound to proteins (such as BSA), dextran, polylysine, or other polymers that adsorb well. Another alternative is to adsorb the polymer on the particles and then couple the hapten or other label. These polyhaptens are used commercially. Another embodiment is to adsorb peptide onto the microspheres and then covalently link more peptide onto the surface.

Also, any polyclonal antibody (PoAb) may also be used to attach the ligand to the particle, such as those from mouse, goat, rabbit, pig, or bovine. These polyclonal antibodies adsorb well and attach to microspheres to form generic microspheres. These then capture any of several poorly adsorbing monoclonal antibodies (MoAb). In theory, a manufacturer can make a series of tests (or assays) from one PoAb preparation.

Some evidence indicates that one can attach 10–40% more protein covalently than by adsorption. When the desired protein coverage is low, covalent coupling may provide more precise control of the coating level. Covalent coupling binds protein more securely, which is an asset in production of tests or assays that are so sensitive that they would be influenced by minute quantities of IgG that might leach off the particles over time. The covalent bond is more thermally stable.

Native silanol groups on the surface of silica microspheres are readily reacted with aqueous or solvent-based silane coupling agents to yield preactivated silica microspheres with a large variety of surface functional groups. Examples include chloromethyl, carboxyl, and amino groups. DNA and RNA are isolated from serum by adsorption onto silica in the presence of chaotropic agents. Oligonucleotides can be covalently bound to surface-modified silica via the 5-amino end. Lipids can be bound via the carboxyl group on the fatty acid chain and propylamine surface groups on the silica.

After the particles have been charged or attached with a ligand, they are then ready to be applied to the skin to remove contaminants therefrom. The particles may either be applied directly to the skin, or they may be coupled with a carrier designed to aid the application of the particles to the skin while reducing the number of particles needed to effectively remove the desired contaminants. The carrier may be any means that permits the effective distribution of the particles over the desired area of the skin. Suitable carriers include, but are not limited to, lotions, creams, sprays, or solutions. Other natural carriers may be used, such as alginate or chitosan. Additionally, the particles may be applied using a non-magnetic cellulosic wipe or a non-magnetic polymeric wipe which is wiped across the surface of the skin.

The amount of particles added to the carrier depends on several factors including the carrier used, the contaminants to be removed and the amount of contaminants, among other factors. In general, from about 0.001 to about 10 mg, or from about 0.1 to about 1.0 mg, of particles may be included per milliliter of carrier.

As a counterpart to the magnetic element included in the particles, the system includes a magnet to attract and remove the magnetized particles from the skin. The magnet or magnets are incorporated into a product, such as a personal care item. The type of product used to magnetically attract and remove the particles may vary, depending on the contaminant to be removed and the surface area to be treated.

The magnets used in the system are selected so as to be incorporated into the personal care product or other article in such a way that they can effectively remove the magnetic particles. The magnets may be incorporated into both woven and non-woven materials, depending on the product. Additionally, the woven and non-woven materials may be composed of natural or synthetic fibers, or a mixture of both. For example, in one embodiment, the magnets may be incorporated into facial tissues, which comprise plant fiber. In another embodiment, the magnets may be incorporated into a non-woven fabric and applied to a disposable article, such as a diaper or a wipe. The magnets may be incorporated into a wide variety of articles, such as bandages, adhesive strips, feminine articles, and adult incontinence products, to name a few more. However, since these various embodiments result in different contact of the product with the skin, the products must be designed accordingly. For facial tissues, the magnets may come into close contact with the skin. Therefore, the number, size and/or strength of the magnets may be different when compared to magnets placed inside a diaper, which do not directly contact the skin, yet must still be able to remove magnetic particles which may have been incorporated into lotion or powder applied to the skin before the diaper was put on.

In one embodiment of the invention, the particles in the system may be colored. By making the particles more visible, the cleaning action of the system can be observed as the particles are applied to the surface and subsequently wiped away. If all of the color is wiped away, there is a presumption that the targeted contaminants have also been wiped away, provided a sufficient amount of the particles had been applied. The color may be applied to the particles in the form of a dye that remains with the particles and does not transfer to other surfaces. The dye may mix with polymers in the particles to prevent the dye from transferring to other surfaces. The concentration of color in the polymer is dependent on the dye, but typically ranges from 0.1% to about 85%.

Examples of suitable types of dyes include acid, azo, basic, direct, disperse, solvent, mordant, reactive, pigment, sulfur, vat, organic, and natural dyes, and combinations of any of these. The most common types of natural dyes are acid or anionic dyes, such as indigo or Tyrian purple. A dye used in the particles may be virtually any color, and in particular, may be either fluorescent or non-fluorescent. Examples of suitable FDC dyes include tartrazine (Yellow #5—lemon yellow), sunset yellow (Yellow #6—orange), erythrosine (Red #3—cherry red), allura red AC (Red #40—orange red), brilliant blue FCF (Blue #1—bright blue), indigotine (Blue #2—royal blue), and fast green FCF (Green #3—sea green). Examples of commercially available fluorescent pigments are found in the line of Fluorescent Pigments 800P Series, available from Chempon Dyes P Ltd of Chicago, Ill. These fluorescent pigments are thermoset fluorescent pigments having a resistance to strong solvents. These pigments are available in a wide range of colors. Examples of commercially available fiber reactive dyes include CIBACRON F and REACTONE, both available from CIBA-Geigy Ltd. of Basle, Switzerland; PROCION MX and PROCION H, both available from ICI of Great Britain; LEVAFIX, available from Bayer Aktiengesellschaft of Germany; DRIMARENE, available from Sandoz Inc. of New York; CAVALITE, available from E. I. Du Pont de Nemours Co. of Wilmington, Del.; PRIMAZIN, available from BASF of Germany; and REMAZOL, available from Hoechst Aktiengesellschaft of Germany.

The present invention also includes methods of removing contaminants from skin using the system of the invention. While it is expected that the system is capable of removing contaminants, such as debris or microbes, from a skin surface, it is also contemplated that the mechanisms described below may also permit the system to be used to remove contaminants from a wide variety of surfaces including, but not limited to, skin, floors, windows, pets, automobiles, watercraft, and counter tops.

In use, means for removing the contaminant are associated with a particle. As previously discussed, these means may involve the attachment of a ligand or generating a charge on the particle. After the means for removing the contaminant are associated with the particle, the particle is then applied to the surface. The particles may either be applied directly, such as using a wipe, or may be included in a carrier which is applied to the surface. After the particles have been applied, the contaminants to be removed bind to the means for removing the contaminant. The particles are then removed from the surface using means for accomplishing the same. When the particle is removed from the surface the contaminant is also removed.

This invention is further illustrated by the following embodiments, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

In one embodiment, the magnetic particles may be placed in a carrier, such as a cream, lotion, spray or solution, and applied to an open wound. These particles could be associated with a ligand capable of removing bacteria from the wound. Magnets could be located in a piece of gauze or a bandage which is wrapped around the wound. Once the bandage contacts the wound, the magnets would pull the magnetic particles and contaminants from the wound. In a similar manner, the particles may be associated with a charge or another ligand and used to treat a variety of different rashes or infections.

In another embodiment, the magnetic particles may be associated with a ligand or charge that is capable of binding to microbes existing in bodily wastes. Such particles may be applied to a baby, for example, using a baby wipe, powder or lotion. The particles would bind with the microbes. A diaper having magnets contained therein may then be placed on the baby, wherein the magnets would remove the magnetic particles and contaminants from the skin of the baby, helping to prevent rashes. Similar embodiments may be used with feminine articles or adult incontinence devices.

In still another embodiment, the particles may be used to help clear pores and prevent breakouts of the skin. The particles could be associated with a ligand or charge that is capable of binding to debris or microbes existing on the skin surface. The particles may be included in a carrier such as a cream or lotion. The particles may be applied to the skin surface via the carrier whereupon they bind with the debris or microbes. An adhesive strip having magnets contained therein may then be applied to the skin. When the strip is removed, the magnetic particles and contaminants would also be removed, helping to clear the pores. Alternatively, a facial wipe may be used in lieu of the adhesive strip.

In still another embodiment, the particles may be used to relieve symptoms associated with sinus problems. Irritation of the skin around the nose may be associated with microbes in the mucous. To remove these microbes, particles having a suitable ligand or charge may be applied to the nose using a carrier such as cream, lotion, or facial tissue. The particles and the microbes bound thereto may then be removed using another facial tissue having magnets contained therein.

As can be seen, the particles of the present invention may be used in many different embodiments depending upon the contaminant to be removed, the surface being treated, the carrier used, and the means for removing the particles and contaminants. It should be understood, of course, that the foregoing embodiments relate only to some of the preferred embodiments of the present invention and that numerous modifications or alterations may be made therein without departing from the spirit and the scope of the invention as set forth in the appended claims.

EXAMPLES

In the Examples, ex-vivo skin test strips were prepared. These strips were then used to determine the effectiveness of the present invention at removing *C. albicans* or *E. coli* from skin. FIG. 1 outlines the magnetic removal protocol used for these Examples. The Examples were performed as follows:

Procedure:
1. Make tape strips, 5 pulls per tape strip on forearm.
2. Place tape strips in wells of 6 well plate.
3. Block with 2.0 ml 5% Bovine Serum Albumin (BSA) in Phosphate Buffered Saline (PBS), pH 7.2.
4. Incubate 30–32° C., 100 RPM, 1 hr.
5. Aspirate wells of 6 well plate dry.
6. Wash tape strip with Tris Buffered Saline (TBS pH) 7.4+0.5% BSA, holding tape strip with tweezers, use eye-dropper to flush tape strip twice.
7. Add 1.0 ml ($10^6$ CFU/ml) *C. albicans* or *E. coli* in TBS pH 7.4 to each well.
8. Add 1.0 ml Typtic Soy Broth (TSB) to each well.
9. Incubate 30–32° C., 100 RPM, 1 hr.
10. Aspirate wells of 6 well plate dry.
11. Wash tape strip with TBS pH 7.4+0.5% BSA, holding tape strip with tweezers, use eye-dropper to flush tape strip twice.
12. Add 2.0 ml 1/200 Rabbit anti-*C. albicans*-Horseradish Peroxidase (HRP) or Rabbit anti-*E.coli*-HRP in TBS pH 7.4+0.5% BSA.
13. Incubate 28–30° C., 100 RPM, 1 hr.
14. Add 2.0 ml 1/200 Sheep anti-rabbit-paramagnetic bead in TBS pH 7.4+0.5% BSA.
15. Incubate 28–30° C., 100 RPM, 1 hr.
16. Wash tape strip with TBS pH 7.4+0.5% BSA, holding tape strip with tweezers, use eye-dropper to flush tape strip twice.
17. Place tape strip in new 6 well plate.
18. Place magnet on surface of tape strip.
19. Remove magnet after 3.0 min.
20. Wash tape strip with TBS pH 7.4, holding tape strip with tweezers, use eye-dropper to flush tape strip twice.
21. Place tape strip in new 6 well plate.
22. Add 2.0 ml peroxidase substrate (ABTS).
23. Incubate 28–30° C., 100 RPM, 15–30 min, read absorbency at 405 nm.
24. Alternative measure of *C. albicans* is to fix the tape strip with 2.5% Gluteraldhye after step 11.
25. Wash tape strip with TBS pH 7.4, holding tape strip with tweezers, use eyedropper to flush tape strip twice.
26. Stain with Calcoflour white.
27. Visually enumerate yeast using fluorescent microscope.

Table 1 outlines the effectiveness of the present invention at magnetically removing *C. albicans* attached to skin.

TABLE 1

| Treatment of Skin with Attached Yeast | HRP Activity ABS 405 nm | % Removal of HRP Activity |
|---|---|---|
| No Treatment | 1.055 | |
| No Treatment | 0.844 | |

TABLE 1-continued

| Treatment of Skin with Attached Yeast | HRP Activity ABS 405 nm | % Removal of HRP Activity |
|---|---|---|
| Plastic Film | 0.802 | 15.5 |
| Magnet Covered with Plastic Film | 0.350 | 63.2 |

Figure 2:
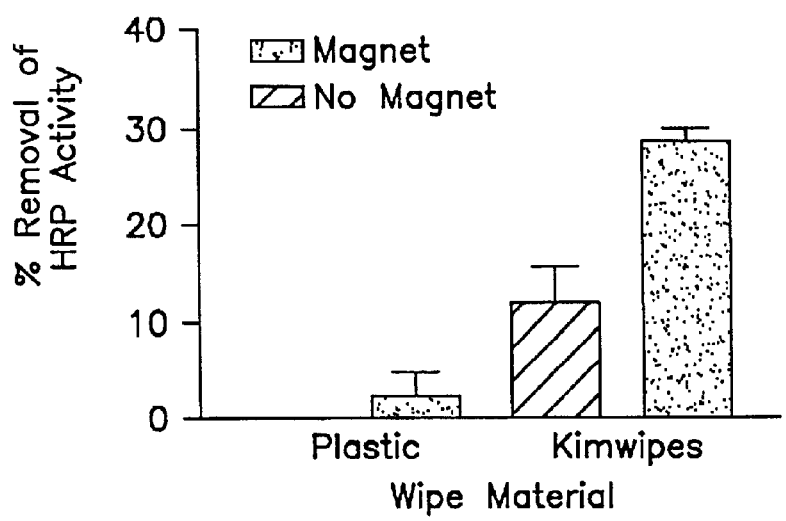
FIG. 2 is a graphical representation of the effectiveness of the present invention at removing *E. coli* attached to skin.
Figure 3:
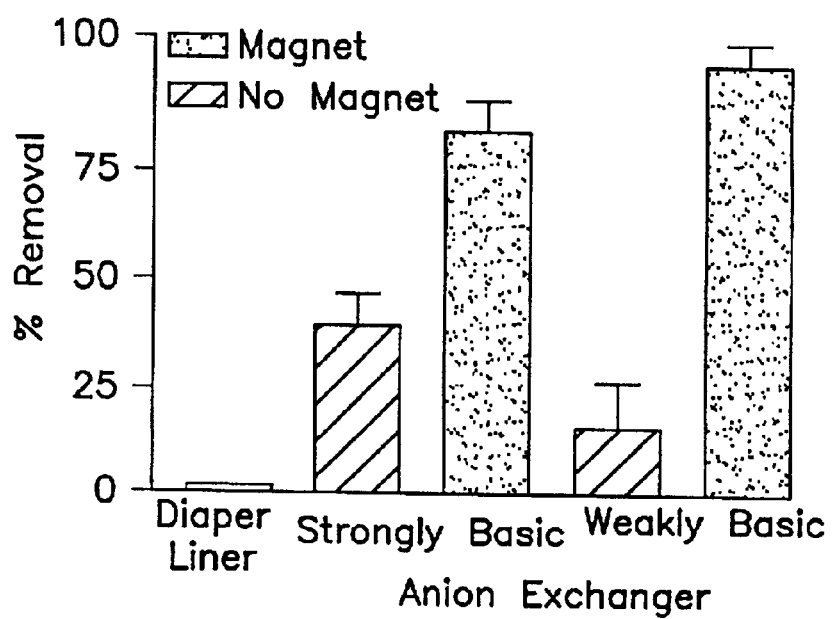
FIG. 3 a graphical representation of the effectiveness of the present invention at removing *C. albicans* from skin using Magnetic Cellulose Particles.

FIGS. 2 and 3 show the effectiveness of the present invention at removing *E. Coli* and *C. albicans* respectively. As can be seen, the use of the magnetic particle greatly enhances the removal of contaminants from a surface such as skin.

Therefore, as these Examples indicate, the present invention offers a highly effective means for removing contaminants from a surface by utilizing a magnetic particle having means attached thereto to selectively remove the surface contaminant. Additionally, the present invention provides for methods of removing surface contaminants using these magnetic particles and means for removing the magnetic particles from the surface.

What is claimed is:

1. A system for removing a contaminant from a skin surface comprising:
    a particle having a magnetic element and means on the particle for selectively binding a contaminant on the skin surface, the particle having a diameter of between about 0.01 and about 20 microns;
    a carrier for applying the particle directly to the skin surface;
    a magnet; and
    a personal care product having the magnet contained therein, for placing the magnet sufficiently adjacent the skin surface such that the particle and the bound contaminant can be removed from the skin surface by exposure to the magnet.

2. The system of claim 1, wherein the particle has a diameter of between about 0.0 1–10 microns.

3. The system of claim 1, wherein the magnetic element comprises iron and the particle comprises between about 1% to 90% by weight of iron.

4. The system of claim 1, wherein the magnetic element comprises iron and the particle comprises between about 10% to 80% by weight of iron.

5. The system of claim 1, wherein the magnetic element comprises cerium and the particle comprises between about 1% to 90% by weight of cerium.

6. The system of claim 1, wherein the magnetic element comprises cerium and the particle comprises between about 10% to 80% by weight of cerium.

7. The system of claim 1, wherein the particle further comprises a dye.

8. The system of claim 7, wherein the dye comprises a fluorescent dye.

9. The system of claim 7, wherein the dye comprises a non-fluorescent dye.

10. The system of claim 7, wherein the dye is selected from a group consisting of acid, azo, basic, direct, disperse, solvent, mordant, reactive, pigment, sulfur, vat, organic, and natural dyes, and combinations thereof.

11. The system of claim 1, wherein the personal care product comprises a nonwoven fabric having the magnet contained therein.

12. The system of claim 1, wherein the personal care product comprises a woven material having the magnet contained therein.

13. The system of claim 1, wherein the personal care product comprises a bandage having the magnet contained therein.

14. The system of claim 1, wherein the personal care product comprises a diaper having the magnet contained therein.

15. The system of claim 1, wherein the personal care product comprises an adhesive strip having the magnet contained therein.

16. The system of claim 1, wherein the personal care product comprises a facial tissue having the magnet contained therein.

17. The system of claim 1, wherein the personal care product comprises a wipe having the magnet contained therein.

18. The system of claim 1, wherein the personal care product comprises a feminine care article having the magnet contained therein.

19. The system of claim 1, wherein the personal care product comprises an adult incontinence article having the magnet contained therein.

20. A system for removing a contaminant from a skin surface comprising:
    a particle including between about 1% to 90% by weight of iron, and means on the particle for selectively binding a contaminant on the skin surface;
    a carrier for applying the particle directly to the skin surface;
    a magnet; and
    a personal care product having the magnet contained therein, for placing the magnet sufficiently adjacent the skin surface such that the particle and the bound contaminant can be removed from the skin surface by exposure to the magnet.

21. The system of claim 20, wherein the particle comprises between about 10% to 80% by weight of iron.

22. The system of claim 20, wherein the particle has a diameter of less than about 25 microns.

23. The system of claim 20, wherein the particle has a diameter of between about 0.01–20 microns.

24. The system of claim 20, wherein the particle has a diameter of between about 0.01–10 microns.

25. The system of claim 20, wherein the particle further comprises a dye.

26. The system of claim 25, wherein the dye comprises a fluorescent dye.

27. The system of claim 25, wherein the dye comprises a non-fluorescent dye.

28. The system of claim 25, wherein the dye is selected from a group consisting of acid, azo, basic, direct, disperse, solvent, mordant, reactive, pigment, sulfur, vat, organic, and natural dyes, and combinations thereof.

29. The system of claim 20, wherein the personal care product comprises a nonwoven fabric having the magnet contained therein.

30. The system of claim 20, wherein the personal care product comprises a woven material having the magnet contained therein.

31. The system of claim 20, wherein the personal care product comprises a bandage having the magnet contained therein.

32. The system of claim 20, wherein the personal care product comprises a diaper having the magnet contained therein.

33. The system of claim 20, wherein the personal care product comprises an adhesive strip having the magnet contained therein.

34. The system of claim 20, wherein the personal care product comprises a facial tissue having the magnet contained therein.

35. The system of claim 20, wherein the personal care product comprises a wipe having the magnet contained therein.

36. The system of claim 20, wherein the personal care product comprises a feminine care article having the magnet contained therein.

37. The system of claim 20, wherein the personal care product comprises an adult incontinence article having the magnet contained therein.

38. A system for removing a contaminant from a skin surface comprising:
- a particle including a dye, a magnetic element, and means on the particle for selectively binding a contaminant on the skin surface;
- a carrier for applying the particle directly to the skin surface;
- a magnet; and
- a personal care product having the magnet contained therein, for placing the magnet sufficiently adjacent the skin surface such that the particle and the bound contaminant can be removed from the skin surface by exposure to the magnet.

39. The system of claim 38, wherein the dye comprises a fluorescent dye.

40. The system of claim 38, wherein the dye comprises a non-fluorescent dye.

41. The system of claim 38, wherein the dye is selected from a group consisting of acid, azo, basic, direct, disperse, solvent, mordant, reactive, pigment, sulfur, vat, organic, and natural dyes, and combinations thereof.

42. The system of claim 38, wherein the particle has a diameter of less than about 25 microns.

43. The system of claim 38, wherein the particle has a diameter of between about 0.01–20 microns.

44. The system of claim 38, wherein the particle has a diameter of between about 0.01–10 microns.

45. The system of claim 38, wherein the magnetic element comprises iron and the particle comprises between about 1% to 90% by weight of iron.

46. The system of claim 38, wherein the magnetic element comprises iron and the particle comprises between about 10% to 80% by weight of iron.

47. The system of claim 38, wherein the magnetic element comprises cerium and the particle comprises between about 1% to 90% by weight of cerium.

48. The system of claim 38, wherein the magnetic element comprises cerium and the particle comprises between about 10% to 80% by weight of cerium.

49. The system of claim 38, wherein the personal care product comprises a nonwoven fabric having the magnet contained therein.

50. The system of claim 38, wherein the personal care product comprises a woven material having the magnet contained therein.

51. The system of claim 38, wherein the personal care product comprises a bandage having the magnet contained therein.

52. The system of claim 38, wherein the personal care product comprises a diaper having the magnet contained therein.

53. The system of claim 38, wherein the personal care product comprises an adhesive strip having the magnet contained therein.

54. The system of claim 38, wherein the personal care product comprises a facial tissue having the magnet contained therein.

55. The system of claim 38, wherein the personal care product comprises a wipe having the magnet contained therein.

56. The system of claim 38, wherein the personal care product comprises a feminine care article having the magnet contained therein.

57. The system of claim 38, wherein the personal care product comprises an adult incontinence article having the magnet contained therein.

58. A system for removing a contaminant from a skin surface comprising:
- a particle including a dye, between about 1% to about 90% by weight of iron, and means on the particle for selectively binding a contaminant on the skin surface, the particle having a diameter of between about 0.01 and about 20 microns;
- a carrier for applying the particle directly to the skin surface;
- a magnet; and
- a personal care product having the magnet contained therein, for placing the magnet sufficiently adjacent the skin surface such that the particle and the bound contaminant can be removed from the skin surface by exposure to the magnet.

59. The system of claim 58, wherein the particle has a diameter of between about 0.01–10 microns.

60. The system of claim 58, wherein the particle comprises between about 10% to 80% by weight of iron.

61. The system of claim 58, wherein the dye comprises a fluorescent dye.

62. The system of claim 58, wherein the dye comprises a non-fluorescent dye.

63. The system of claim 58, wherein the dye is selected from a group consisting of acid, azo, basic, direct, disperse, solvent, mordant, reactive, pigment, sulfur, vat, organic, and natural dyes, and combinations thereof.

64. The system of claim 58, wherein the personal care product comprises a nonwoven fabric having the magnet contained therein.

65. The system of claim 58, wherein the personal care product comprises a woven material having the magnet contained therein.

66. The system of claim 58, wherein the personal care product comprises a bandage having the magnet contained therein.

67. The system of claim 58, wherein the personal care product comprises a diaper having the magnet contained therein.

68. The system of claim 58, wherein the personal care product comprises an adhesive strip having the magnet contained therein.

69. The system of claim 58, wherein the personal care product comprises a facial tissue having the magnet contained therein.

70. The system of claim 58, wherein the personal care product comprises a wipe having the magnet contained therein.

71. The system of claim 58, wherein the personal care product comprises a feminine care article having the magnet contained therein.

72. The system of claim 58, wherein the personal care product comprises an adult incontinence article having the magnet contained therein.

* * * * *

UNITED STATES PATENT AND TRADEMARK OFFICE
CERTIFICATE OF CORRECTION

PATENT NO. : 6,841,393 B2
DATED : January 11, 2005
INVENTOR(S) : David W. Koenig It is certified that error appears in the above-identified patent and that said Letters Patent is hereby corrected as shown below:

Title page,
Item [*] Notice, insert the following:
-- This patent is subject to a Terminal Disclaimer. --.

Signed and Sealed this

Sixteenth Day of August, 2005

JON W. DUDAS
*Director of the United States Patent and Trademark Office*